United States Patent [19]

Feiring

[11] 4,157,344

[45] Jun. 5, 1979

[54] PREPARATION OF ARYL TRIFLUOROMETHYL ETHERS

[75] Inventor: Andrew E. Feiring, Wilmington, Del.

[73] Assignee: E. I. Du Pont de Nemours and Company, Wilmington, Del.

[21] Appl. No.: 870,022

[22] Filed: Jan. 16, 1978

[51] Int. Cl.$^2$ .................... C07C 85/00; C07C 41/00
[52] U.S. Cl. ................................ 260/575; 260/465 F; 260/465 G; 260/591; 568/584; 568/585; 568/586; 568/587; 568/588
[58] Field of Search .............. 260/612 D, 575, 465 F, 260/465 G, 591, 613 D; 568/584, 585, 586, 587, 588

[56] References Cited

FOREIGN PATENT DOCUMENTS 765527  1/1957  United Kingdom ................ 260/612 D

OTHER PUBLICATIONS

Sheppard, J.A.C.S., vol. 83, No. 23 (1961) pp. 4860–4861.

*Primary Examiner*—Bernard Helfin

[57] ABSTRACT

A one-step process for the synthesis of aryl trifluoromethyl ethers by reacting phenol or certain substituted phenols with a perhalomethane and hydrogen fluoride is provided. The compounds produced by the process of this invention are useful intermediates in the production of dyestuffs and pharmaceuticals.

3 Claims, No Drawings

PREPARATION OF ARYL TRIFLUOROMETHYL ETHERS

BACKGROUND OF THE INVENTION

1. Field of the Invention

A process is disclosed for the synthesis of aryl trifluoromethyl ethers by reacting phenol or certain substituted phenols with a perhalomethane and hydrogen fluoride.

2. Relation to the Prior Art

W. A. Sheppard, J. Org. Chem., 29, 1 (1964) discloses the two-step preparation of aryl trifluoromethyl ethers by the reaction of aryl fluoroformates with sulfur tetrafluoride ($SF_4$). The aryl fluoroformates are prepared in situ from phenols and carbonyl fluoride ($COF_2$). The hydrogen fluoride generated in this reaction catalyzes the $SF_4$ reaction. The two-step process is represented by the following reactions:

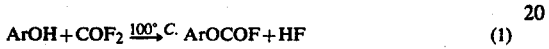

(1)

(2)

French Pat. No. 2,214,674 discloses a two-step process of preparation of aryl trifluoromethyl ethers by the reaction of molybdenum hexafluoride ($MoF_6$) with aryl chlorothioformates. This process is represented by the following reactions:

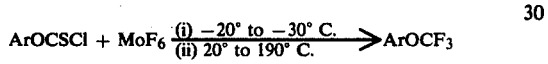

F. Mathey and J. Bensoam, Tetrahedron Letters, 2253 (1973) discloses the same process of French Pat. No. 2,214,674. The reactant aryl chlorothioformates are prepared from the corresponding phenols by treatment of their sodium salts with thiophosgene as follows:

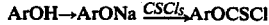

N. N. Iarovenko and A. S. Vasil'eva, J. Gen. Chem. USSR 28, 2539 (1958) describe the reaction of phenyl trichloromethyl ether with a mixture of antimony trifluorides ($SbF_3$) and antimony pentachloride ($SbCl_5$) to produce phenyltrifluoromethyl ether.

L. M. Yagupolskii, Dokl. Akad. Nauk SSSR, 105. 100 (1955) discloses a process similar to that described in the Iarovenko et al. article for preparing $ArOCF_3$ where Ar is $C_6H_5$, 2—$ClC_6H_4$, 4—$F_6C_6H_4$, 2,4—$Cl_2C_6H_3$, 4—$CNC_6H_4$, 4—$H_2NC_6H_4$, 4—$HO_2CC_6H_4$ and 4—$H_2NCOC_6H_4$.

British Pat. No. 765,527 claims the process of manufacture of aryl trifluoromethyl ethers by treatment with hydrogen fluoride at elevated temperatures and pressures according to the reaction:

U.S. Pat. No. 4,020,112 describes the formation of various fluorinated products, including diaryl ethers, from the reaction of phenols with HF and $SF_4$. Aryl trifluoromethyl ethers are not among the products of this reaction.

SUMMARY OF THE INVENTION

The present invention provides a method for the preparation of aryl trifluoromethyl ethers (substituted trifluoromethoxybenzenes) comprising reacting:

(1) a phenolic compound of the formula

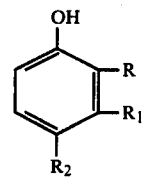

wherein, independently,

R is H, Cl, F or Br;

$R_1$ is H, Cl, Br, F, $NO_2$, $NH_2$, CN, $CF_3$, alkyl containing 1–4 carbon atoms, phenyl or benzoyl; and $R_2$ is H, Cl, Br, F, $NO_2$, $NH_2$, CN, $CF_3$, alkyl containing 1–4 carbon atoms, phenyl, benzoyl or OH with (2) at least one equimolar amount of a perhalomethane selected from the group consisting of $CCl_4$, $CFCl_3$ or $CBrCl_3$ and (3) at least three molar equivalents of substantially anhydrous hydrogen fluoride in the temperature range of about 80° to about 175° C. under autogenous pressure to produce an aryl trifluoromethyl ether of the general formula

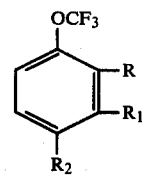

A preferred process for the preparation of aryl trifluoromethyl ethers comprises reacting:

(1) a phenolic compound of the formula

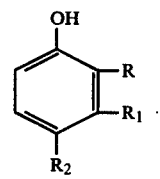

wherein, independently,

R is H, Cl, F or Br;

$R_1$ is H, Cl, Br, F, $NO_2$, $NH_2$, CN, $CF_3$, alkyl containing 1–4 carbon atoms, phenyl or benzoyl, and $R_2$ is H, Cl, Br, F, $NO_2$, $NH_2$, CN, $CF_3$, alkyl containing 1–4 carbon atoms, phenyl or benzoyl with (2) a perhalomethane selected from the group consisting of $CCl_4$, $CFCl_3$ or $CBrCl_3$, said perhalomethane being present in an amount of 2–3 moles per mole of the phenolic compound, and (3) from 20–45 moles of substantially anhydrous hydrogen fluoride per mole of phenolic compound, the reaction being carried out in the temperature range of 125°–150° C. under autogeneous pressure to produce an aryl trifluoromethyl ether of the general formula

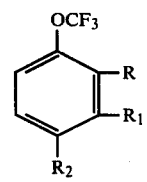

In an especially preferred process the phenolic compounds are selected from 3-nitrophenol, 4-nitrophenol, 4-chlorophenol, 4-aminophenol, and 2,4-dichlorophenol and the perhalomethane is carbon tetrachloride.

DETAILED DESCRIPTION OF THE INVENTION

The process of this invention gives the desired aryl trifluoromethyl ethers in a single step starting with inexpensive and readily available reagents which can be reacted under substantially anhydrous conditions and autogeneous pressure.

The phenolic reagent employed in this process is a phenol which optionally has substituted thereon one or more groups which are resistant to the action of anhydrous hydrogen fluoride under reaction conditions. The substituents which can be present in the ortho, meta or para positions relative to the phenyl hydroxyl group, include chlorine, fluorine and bromine. Alternative substituent groups which can be present in the meta or para positions include nitro, cyano, alkyl of one to four carbon atoms, phenyl, amino, benzoyl and trifluoromethyl groups.

Additionally hydroquinone, which is optionally substituted with one or more of the previously mentioned substituent groups, can be employed in this process to yield mono or bis (trifluoromethoxy) derivatives.

The preferred phenolic compounds for this process are 3- and 4-nitrophenol, 4-chlorophenol, 4-aminophenol and 2,4-dichlorophenol.

The trifluoromethylating agent used in this process is a mixture of substantially anhydrous hydrogen fluoride and a perhalomethane selected from the group comprising carbon tetrachloride, fluorotrichloromethane or bromotrichloromethane.

In carrying out the process of this invention, the reaction vessel should be constructed of materials which are resistant to hydrogen fluoride at the temperature of the reaction. Suitable materials include metal alloys such as Hastelloy and plastics such as polytetrafluoroethylene. A closed vessel is generally employed to minimize the loss of volatile reagents, and the reaction can be run under autogenous pressure. A portion of the HCl formed during the reaction can be vented so long as sufficient pressure is maintained to keep most of the hydrogen fluoride in the liquid state during reaction.

The mole ratio of reactants to achieve high yield requires at least one equivalent of the perhalomethane for each trifluoromethoxy group to be introduced. An excess (2- to 3-fold) of the perhalomethane is employed to maximize the yield. Hydrogen fluoride is both a reactant and the preferred solvent for the reaction, and at least 3 equivalents of HF for each trifluoromethoxy group to be introduced is required and an excess of HF (20–45 moles per mole substrate) is preferably employed to maximize the yield.

The reactions can be conducted by introducing the phenolic compound, perhalomethane and hydrogen fluoride into a reaction vessel which is cooled in dry ice and evacuated prior to the introduction of HF. The vessel is sealed and raised to the reaction temperature and shaken or stirred for a length of time sufficient to cause the reaction to occur. For reactions run under autogeneous pressure, the pressure increase caused by the formation of HCl can be used to monitor the course of the reaction.

The product can be isolated by a variety of techniques. The preferred method involves evaporating the HF, dissolving the residue in an inert solvent such as dichloromethane, ethyl ether or fluorotrichloromethane, washing with dilute aqueous caustic to remove unreacted phenol and isolating the product from the organic solvent by conventional techniques.

The reaction can be conducted at temperatures of about +80° C. to about +175° C. The preferred range is 125°–150°.

The trifluoromethoxyaromatic compounds produced by this process are stable, water insoluble materials which are useful intermediate products in the production of dyestuffs (British Pat. No. 765,527, L. M. Yagupolskii and M. S. Marenets, J. Gen. Chem. USSR 27, 1477 (1957)) and pharmaceuticals (U.S. Pat. No. 3,021,368 (1962); French Pat. No. 1,245,552 (1960)). The trifluoromethoxy group is stable to normal chemical transformation of the aromatic ring such as reduction, aromatic substitution and various functional group transformations (W. A. Sheppard, J. Org. Chem. 29, 1 (1964)).

SPECIFIC EMBODIMENTS OF THE INVENTION

The following examples illustrate specific embodiments of the invention. Unless otherwise indicated, percentages are weight percents, temperatures are in degrees Centigrade and in the reaction mechanisms described the reaction products, other than the aryl trifluoromethyl ethers, are omitted for convenience.

EXAMPLE 1

4-Nitrophenyl trifluoromethyl ether was prepared according to the following reaction:

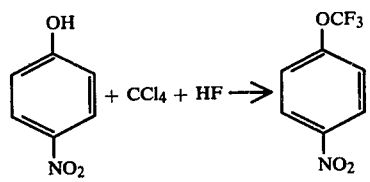

An 80 ml Hastelloy C bomb was charged with 7.0 g (0.05 mole) of 4-nitrophenol and 23 g (0.15 mole) of carbon tetrachloride. The bomb was closed, cooled in dry ice and acetone and charged with 40 g of hydrogen fluoride. The bomb contents were agitated for 2 hr at 100° and then for 8 hr at 150°. The bomb was cooled to 25°–30°, vented for 2 hr and opened. The contents were rinsed from the bomb with two 50 ml portions of methylene chloride. The combined methylene chloride solutions were extracted with 200 ml of 5% KOH in water, dried over anhydrous calcium chloride and concentrated using a rotary evaporator to 6.5 g of dark oil. Distillation of the oil gave 5.83 g of 4-nitrophenyl trifluoromethyl ether having a boiling point of 40°–42° at 0.4 mm; nmr (δ, CDCl$_3$) 7.84 (aromatic quartet); fluorine nmr (δ, CDCl$_3$) −58.41 (s).

The alkaline extract was acidified with cold concentrated hydrochloric acid and extracted with ethyl ether to give 1.4 g of recovered 4-nitrophenol after drying (CaCl$_2$) and concentration in a rotary evaporator.

EXAMPLE 2

4-Chlorophenyl trifluoromethyl ether was prepared according to the following reaction:

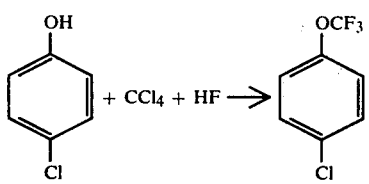

A 1200 ml Hastelloy C autoclave was charged with 77.1 g (0.6 mole) of 4-chlorophenol and 277.2 g (1.8 mole) of carbon tetrachloride. The vessel was cooled in dry ice/acetone, evacuated and charged with 400 g (20 mole) of HF. The mixture was agitated at 150° for 8 hr. The mixture was then cooled to room temperature, quenched by injection of 300 g of water and the contents of the autoclave were poured into a polyethylene vessel. The autoclave was rinsed twice with 100 ml ethyl ether. The ether rinses were added to the polyethylene vessel, and the mixture was diluted with an additional 500 ml of ether and stirred vigorously for ½ hr. The ether layer which formed was separated and extracted with 100 ml portions of 5% aqueous KOH until an extract remained alkaline. The ether solution was dried over anhydrous MgSO₄, filtered and the ether was removed by distillation at atmospheric pressure. The residue was distilled and yielded 79.1 g (67% conversion) of 4-chlorophenyl trifluoromethyl ether having a boiling point of 142°–145°; proton nmr ($\delta$, CDCl₃) 7.20 (quartet); and fluorine nmr ($\delta$, CDCl₃) –58.76 (singlet).

EXAMPLE 3

4-Chlorophenyl trifluoromethyl ether was prepared as in Example 2 according to the following:

An 80 ml Hastelloy C bomb was charged with 6.4 g (0.05 mole) of 4-chlorophenol and 7.7 g (0.05 mole) of carbon tetrachloride. The bomb was cooled in dry ice and acetone, evacuated and charged with 20 g (1 mole) of HF. The mixture was agitated for 8 hr at 150°, then cooled to room temperature and vented to the atmosphere. The mixture was poured into a plastic bottle and the bomb was rinsed twice with 50 ml portions of methylene chloride which were added to the product mixture. The mixture was then treated with sodium fluoride powder to remove the excess HF, filtered and extracted with 100 ml of 5% aqueous NaOH, dried over anhydrous calcium chloride and concentrated by atmospheric pressure distillation. The residue weas distilled under aspirator vacuum to give 5.42 g of 4-chlorophenyl trifluoromethyl ether contaminated with a small amount of methylene chloride. The conversion, corrected for the methylene chloride impurity, was 43%.

EXAMPLE 4

4-Aminophenyl trifluoromethyl ether was prepared according to the following reaction:

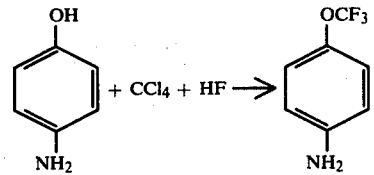

An 80 ml Hastelloy C bomb was charged with 6.05 g (0.05 mole) of 4-aminophenol and 23 g (0.15 mole) of carbon tetrachloride. The bomb was closed, cooled in dry ice and acetone and charged with 40 g (2 moles) of HF. The mixture was agitated at 150° for 8 hr. The bomb was then cooled to 25°–30° and vented to the atmosphere to allow the excess HF to evaporate. The residue was dissolved in 150 ml water and made alkaline by the addition of 20% KOH in water. This solution was extracted twice with 100 ml methylene chloride. The combined methylene chloride extracts were dried over CaCl₂, filtered and concentrated in a rotary evaporatory to 3.65 g of oil. Distillation of the oil through a short path still gave 3.20 g of 4-aminophenyl trifluoromethyl ether having a boiling point of 35°–36° at 0.6 mm; nmr ($\delta$, CDCl₃) 3.63 (bs, 2H), 6.76 (q, 4H); fluorine nmr ($\delta$, CDCl₃) –58.98 (s).

EXAMPLE 5

3-Trifluoromethylphenyl trifluoromethyl ether was prepared according to the following reaction:

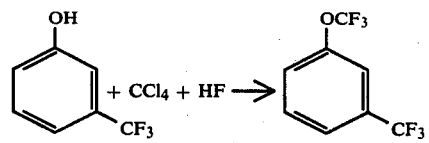

An 80 ml Hastelloy C bomb was charged with 8.1 g (0.05 mole) of 3-hydroxybenzotrifluoride and 23 g (0.15 mole) of carbon tetrachloride. The bomb was closed, cooled in dry ice and acetone and charged with 40 g of HF. The bomb contents were agitated at 150° for 8 hr, then cooled to 0° and poured onto 40 g of ice. The bomb was rinsed with two 40 ml portions of methylene chloride which were added to the ice-water mixture. The methylene chloride layer which formed was separated and the aqueous layer was extracted with 25 ml additional methylene chloride. The methylene chloride solutions were then combined and extracted with 50 ml of 5% aqueous KOH, dried over anhydrous CaCl₂ and filtered. The filtrate was distilled at atmospheric pressure to give, after removing the methylene chloride, 6.8 g (60% conversion) of 3-trifluoromethylphenyl trifluoromethyl ether having a boiling point of 110°–117°; proton nmr ($\delta$, CDCl₃) 7.48 (m); fluorine nmr ($\delta$, CDCl₃) –58.79 (S, 3F, —OCF₃) and –63.67 (S, 3F, —CF₃).

EXAMPLE 6

2,4-Dichlorophenyl trifluoromethyl ether was prepared according to the reaction:

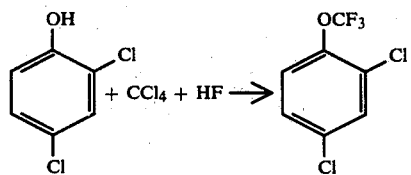

A 200 ml Hastelloy C bomb was charged with 8.2 g (0.05 mole) of 2,4-dichlorophenol and 23 g (0.15 mole) of carbon tetrachloride. The vessel was cooled in dry ice and acetone, evacuated and charged with 40 g of HF. The mixture was agitated for 8 hr at 150°, then cooled to room temperature. The excess HF was removed by aspirator vacuum and the residue was dissolved in 225 ml of methylene chloride. The methylene chloride solution was extracted with 100 ml of 5% KOH in water, dried over CaCl₂ and filtered. The filtrate was concentrated in a rotary evaporator to 9.9 g of liquid. Distillation of the liquid produced 8.4 g of colorless 2,4-dichlorophenyl trifluoromethyl ether having a boiling point of 69°–71° at 25 mm; proton nmr (δ, CDCl₃) 7.25 (S, 2H), 7.45 (t, 1H); fluorine nmr (δ, CDCl₃) –58.71 (S).

EXAMPLE 7

2-Fluorophenyl trifluoromethyl ether was prepared according to the reaction:

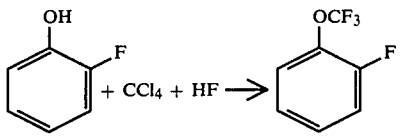

A 200 ml Hastelloy C bomb was charged with 7.84 g (0.07 mole) of 2-fluorophenol and 32 g (0.21 mole) of carbon tetrachloride. The bomb was closed, cooled in dry ice and acetone and charged with 40 g of HF. The mixture was agitated at 150° for 8 hr. The material was cooled in ice water and carefully diluted with 50 ml H₂O and 50 ml fluorotrichloromethane and this mixture was agitated. The lower organic phase which formed was removed, washed with 5% aqueous KOH, dried over anhydrous calcium chloride and filtered. The filtrate was concentrated by distilling off the CFCl₃ at atmospheric pressure. The residue was distilled through a short path condenser to give 4.45 of 2-fluorophenyl trifluoromethyl ether having a boiling point of 103°–105°; proton nmr (δ, CDCl₃) 7.0–7.5 (multiplet); fluorine nmr (δ, CDCl₃) –59.47 (3F, OCF₃), –129.59 (1F, —F).

EXAMPLE 8

3-Nitrophenyltrifluoromethyl ether was prepared according to the reaction:

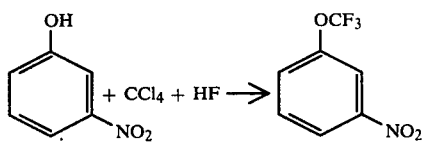

A 1200 ml Hastelloy C bomb was charged with 50 g (0.36 mole) of nitrophenol and 165 g (1.07 mole) of carbon tetrachloride. The bomb was closed, cooled in dry ice and acetone, evacuated and charged with 300 g (15 mole) of HF. The mixture was agitated at 150° for 8 hr. The bomb was cooled to room temperature and the excess HF was removed by aspirator vacuum. The residue was dissolved in 3-200 ml portions of ethyl ether. The combined ether solutions were washed with 20% aqueous KOH until an extract remained alkaline, dried over anhydrous calcium chloride, filtered and concentrated on a rotary evaporator to a dark oil. Distillation of the oil through a short path distillation column gave 52 g (69% conversion) of faintly yellow 3-nitrophenyl trifluoromethyl ether having a boiling point of 51°–54° (0.4 mm); proton nmr (δ, CDCl₃) 7.5–7.7 (multiplet, 2H), 7.9–8.3 (multiplet, 2H); fluorine nmr (δ, CDCL₃) –58.68 (S).

EXAMPLE 9

4-Methylphenyl trifluoromethyl ether was prepared according to the reaction:

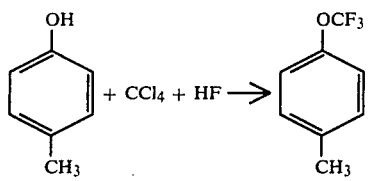

A 1200 ml Hastelloy C bomb was charged with 75.6 g (0.7 mole) of p-cresol and 215.6 g (1.4 mole) of carbon tetrachloride. The vessel was cooled in dry ice and acetone, evacuated and charged with 400 g (20 mole) of HF. The mixture was agitated at 100° for 2 hr, then at 150° for 4 hr. The vessel was cooled to room temperature, vented to atmospheric pressure, water (300 ml) was injected and the mixture was again allowed to cool to room temperature. The mixture was poured into a plastic bottle and the bomb was rinsed twice with 200 ml ethyl ether. The rinses were added to the plastic bottle. After further dilution with 200 ml H₂O and 200 ml ether, the mixture was stirred for 1 hr and an ether layer and an aqueous layer formed. The layers were separated and the ether solution was stirred with 20% aqueous KOH until the solution remained alkaline. The ether layer which formed was collected, dried over anhydrous magnesium sulfate and filtered. The filtrate was distilled through a 6″ Vigroux column to remove the ether. The residue was distilled through a short path column to give 6.7 g 4-methylphenyl trifluoromethyl ether having a boiling point of 130°–135°; proton nmr (δ, CDCl₃) 7.07 (S, 4H), 2.28 (S, 3H); fluorine nmr (δ, CDCl₃) –58.59 (S).

EXAMPLE 10

Phenyl trifluoromethyl ether was prepared according to the reaction:

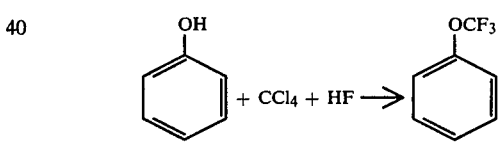

A 10 ml Hastelloy C bomb was charged with 0.94 g (0.01 mole) of phenol and 2.08 g (0.0135 mole) of carbon tetrachloride. The bomb was cooled in dry ice and acetone, evacuated and charged with 4 ml (0.2 mole) of HF, and the bomb was agitated at 100° for 3 hr. The bomb was cooled to room temperature and evacuated through a trap system consisting of a sodium fluoride scrubber and a glass trap cooled in dry ice and acetone. The glass trap was found to contain 1.14 g of colorless liquid. Gas-liquid partition chromatography analysis of the liquid using a 10 ft × ¼ in 10% Carbowax column at 50° indicated the presence of three components which were identified by co-injection with authentic samples as phenyl trifluoromethyl ether, (16%), carbon tetrachloride (61%) and fluorotrichloromethane (23%).

EXAMPLE 11

Example 10 was duplicated except the reaction was carried out at 150° for 3 hr. The reaction product was 0.55 g of liquid phenyl trifluoromethyl ether (33%), carbon tetrachloride (2%) and fluorotrichloromethane (65%).

EXAMPLE 12

4-Cyanophenyl trifluoromethyl ether was prepared according to the reaction:

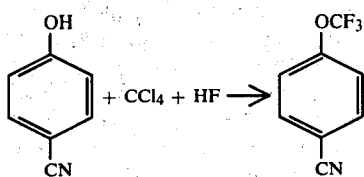

An 80 ml Hastelloy C bomb was charged with 5.95 g (0.05 mole) of 4-cyanophenol and 23 g (0.15 mole) of carbon tetrachloride. The bomb was cooled in dry ice and acetone, evacuated and charged with 40 g of HF. The mixture was agitated at 150° for 8 hr, then cooled to 25°-30° and vented for 2 hr. The product was rinsed from the bomb three times with 50 ml of methylene chloride. The combined methylene chloride extracts were treated with NaF powder, filtered, and extracted with 5% aqueous KOH, dried over anhydrous calcium chloride, and filtered. The filtrate was concentrated in a rotary evaporator to 1.33 g of oil. The flask containing this material was heated in an oil bath to 80° under vacuum and a colorless liquid was collected in a dry ice cooled receiver. The product was 0.4 g of 4-cyanophenyl trifluoromethyl ether having proton nmr ($\delta$, CDCl$_3$) 7.72 (quartet); fluorine nmr ($\delta$, COCl$_3$) -58.31 ppm.

EXAMPLE 13

4-Benzoylphenyl trifluoromethyl ether was prepared according to the following reaction:

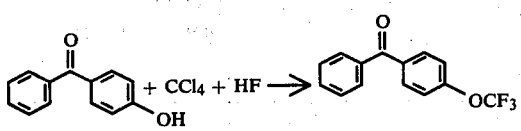

The procedure of Example 12 was employed except that 9.9 g (0.05 mole) of 4-hydroxybenzophenone was reacted in place of the 4-cyanophenol. The reaction yielded 6.2 g of product 4-benzoylbenzyl trifluoromethyl ether, which indicated an OCF$_3$ absorption in the fluorine nmr spectrum at -58.22 ppm.

EXAMPLE 14

4-Phenylphenyl trifluoromethyl ether was prepared according to the reaction:

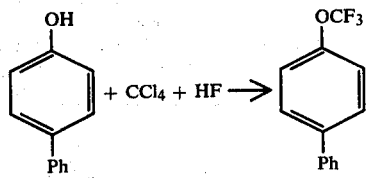

The procedure of Example 12 was employed except that 8.5 g (0.05 mole) of 4-phenylphenol were used in place of the 4-cynophenol. The reaction yielded 0.7 g of material which indicated an OCF$_3$ absorption in the fluorine nmr spectrum at -58.41 ppm.

EXAMPLE 15

4-Chlorophenyl trifluoromethyl ether as in Example 2 was prepared according to the following:

An 80 ml Hastelloy C bomb was charged with 6.43 g (0.05 mole) of 4-chlorophenol and 20.7 g (0.15 mole) of fluorotrichloromethane. The bomb was cooled in dry ice and acetone, evacuated and charged with 40 g (2 mole) of HF. The mixture was agitated at 150° for 8 hr. The mixture was cooled in an ice water bath, vented to the atmosphere and carefully poured over 40 g of ice. The bomb was rinsed with 25 ml of methylene chloride which was then added to the ice water mixture. The lower organic layer which formed was removed, extracted with 5% aqueous KOH, dried over anhydrous calcium chloride and filtered. The filtrate was distilled at atmospheric pressure to give, after removing the methylene chloride, 2.95 g (31%, conversion) of 4-chlorophenyl trifluoromethyl ether.

EXAMPLE 16

4-Nitrophenyl trifluoromethyl ether as in Example 1 was prepared according to the following:

A 200 ml Hastelloy C bomb was charged with 7.0 g (0.05 mole) of 4-nitrophenol and 30 g (0.15 mole) of bromotrichloromethane. The bomb was closed, cooled in dry ice and acetone, evacuated and charged with 50 g of HF. The mixture was agitated at 150° for 8 hr, then cooled to room temperature, and the excess HF was removed by aspiration. The residue was dissolved in 3-100 ml portions of ethyl ether. The combined ether solutions were extracted with 5% aqueous KOH until an extract remained alkaline, dried over anhydrous magnesium sulfate and filtered. The filtrate was concentrated in a rotary evaporator to 2.45 g of oil which had proton and fluorine nmr spectra identical to those obtained in Example 1.

EXAMPLE 17

4-Trifluoromethoxyphenyl trifluoromethyl ether and 4-hydroxyphenyl trifluoromethyl ether were prepared according to the following reaction:

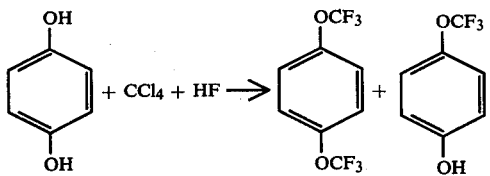

An 80 ml Hastelloy C bomb was charged with 5.5 g (0.05 mole) of hydroquinone and 30.8 g (0.2 mole) of carbon tetrachloride. The bomb was cooled in dry ice-/acetone, evacuated and charged with 30 g (1.5 mole) of HF. The mixture was agitated at 150° for 8 hr, then cooled to 0° and vented to atmospheric pressure. The bomb contents were poured over 50 g of ice. The bomb was rinsed with 30 ml of methylene chloride which was added to the product/ice mixture. The layers which formed were separated and the aqueous solution was extracted with an addition 25 ml methylene chloride. The combined methylene chloride solutions were extracted with 100 ml of 5% aqueous KOH, dried over anhydrous calcium chloride and filtered. The filtrate was distilled under aspirator vacuum to give, after removing the methylene chloride, 5.8 g of colorless 4-trifluoromethoxyphenyl trifluoromethyl ether having proton nmr ($\delta$, CDCl$_3$) 7.23 (S); fluorine nmr ($\delta$, CDCl$_3$) -58.94, contaminated with a trace of methylene chloride. The conversion corrected for the impurity is 36.5%.

The KOH extract was acidified by the addition of concentrated HCl and extracted with 50 ml ethyl ether. The ether solution was dried over anhydrous calcium chloride and concentrated in a rotary evaporator to 1.24 g of oil. Fluorine nmr of the oil indicated a singlet at −59.29 ppm for 4-hydroxyphenyl trifluoromethyl ether.

EXAMPLE 18

2-Chloro-4-trifluoromethoxyphenyl trifluoromethyl ether was prepared according to the reaction:

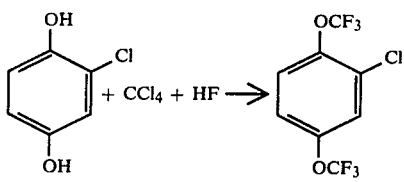

A 200 ml Hastelloy C vessel was charged with 10.1 g (0.07 mole) of chlorohydroquinone and 43 g (0.28 mole) of carbon tetrachloride. The vessel was cooled in dry ice/acetone, evacuated and charged with 50 g of hydrogen fluoride. The mixture was agitated at 150° for 8 hr. The vessel was cooled to room temperature and charged with 50 g of water. After cooling again to room temperature, the mixture was poured into a plastic bottle. The bomb was rinsed twice with 50 ml of fluorotrichloromethane and both rinses were added to the product. The layers which formed were separated and the aqueous layer was extracted with 25 ml of fluorotrichloromethane. The combined organic solutions were extracted with cold 5% aqueous KOH, dried over anhydrous calcium chloride and filtered. The solvent was removed and the remaining product was distilled through a short path column under aspirator vacuum to give 2.9 g of colorless liquid having a boiling point of 35°–50°. Glpc analysis of the liquid using a 10 ft×¼ in 10% Carbowax column at 150° indicated three peaks with retention times of 1.8, 2.0 and 3.8 min. The second peak was identified as the desired 2-chloro-4-trifluoromethoxy phenyl trifluoromethyl ether by mass spectroscopy.

EXAMPLE 19

4-Nitrophenyl trifluoromethyl ether was prepared according to the following reaction:

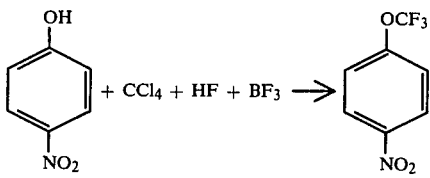

A 1-liter stirred Hastelloy C autoclave was charged with 83.4 g (0.6 mole) of 4-nitrophenol and 277 g (1.8 mole) of carbon tetrachloride. The autoclave was closed, cooled with dry ice and acetone, evacuated and charged with 350 g of HF. Boron trifluoride (10 g) was then added. The mixture was stirred and heated at 130° for 8 hr. The mixture was cooled to room temperature and the HF was removed by aspirator. Two 300 ml portions of methylene chloride were used to rinse the product into a plastic bottle. Anhydrous sodium fluoride (¼ lb, 113.5 g) was added and the mixture was stirred for 1 hr. This mixture was filtered and the filtrate was concentrated on a rotary evaporator to remove the methylene chloride. The dark residue produced was diluted with 500 ml 5% aqueous KOH and distilled. A total of 500 ml of distillate was collected in 100 ml portions with an additional 250 ml of water being added during distillation. Each portion of the distillate was transferred to a separatory funnel. A lower organic layer was separated. The aqueous layers were each extracted with 30 ml methylene chloride. The combined organic material from all portions was dried over anhydrous MgSO₄, filtered, and concentrated using a rotary evaporator to remove the methylene chloride leaving 95 g (0.46 mole, 76%) of 4-nitrophenyl trifluoromethyl ether as a faintly yellow oil.

EXAMPLE 20

4-Nitrophenyl trifluoromethyl ether was prepared according to the following reaction:

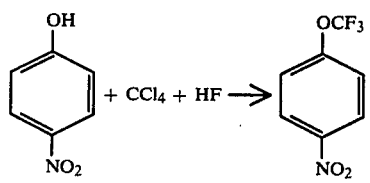

This Example was a duplicate of Example 19 except that no BF₃ was added. In this Example 36.2 g (0.17 mole, 28%) of 4-nitrophenyl trifluoromethyl ether were produced. Comparison of this Example with Example 19 shows improved yields obtainable using BF₃ as a catalyst.

The foregoing examples are intended to illustrate this invention but not limit it in any way. In particular, this invention is contemplated to also include, inter alia, preparation of the aryl trifluoromethyl ethers listed in Table I.

TABLE I

| Example | Phenol | Product |
|---|---|---|
| 21 | 4-Bromophenol | 4-Bromophenyl trifluoromethyl ether |
| 22 | 3-Bromophenol | 3-Bromophenol trifluoromethyl ether |
| 23 | 2-Bromophenol | 2-Bromophenyl trifluoromethyl ether |
| 24 | 2-Chlorophenol | 2-Chlorophenyl trifluoromethyl ether |
| 25 | 3-Chlorophenol | 3-Chlorophenyl trifluoromethyl ether |
| 26 | 3-Chloro-4-methylphenol | 3-Chloro-4-methylphenyl trifluoromethyl ether |
| 27 | 4-Chloro-3-methylphenol | 4-Chloro-3-methylphenyl trifluoromethyl ether |
| 28 | 2-Chloro-4-methylphenol | 2-Chloro-4-methylphenyl trifluoromethyl ether |
| 29 | 3-Methyl-4-nitrophenol | 3-Methyl-4-nitrophenol trifluoromethyl ether |
| 30 | 4-Methyl-3-nitrophenol | 4-Methyl-3-nitrophenyl trifluoromethyl ether |
| 31 | 4-Ethylphenol | 4-Ethylphenol trifluoromethyl ether |
| 32 | 3-Ethylphenol | 3-Ethylphenol trifluoromethyl ether |
| 33 | 3-Aminophenol | 3-Aminophenyl trifluoromethyl ether |

I claim:

1. The process of preparing an aryl trifluoromethyl ether of the general formula:

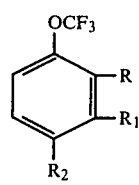

comprising reacting in the temperature range of about 80° to about 175° C. and under sufficient pressure to keep most of the hydrogen fluoride in the liquid state the following:

(a) a phenolic compound of the formula

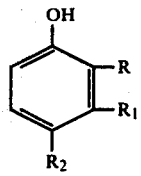

wherein, independently,

R is H, Cl, F or Br;

R$_1$ is H, Cl, Br, F, NO$_2$, NH$_2$, CN, CF$_3$, alkyl containing 1–4 carbon atoms, phenyl or benzoyl; and R$_2$ is H, Cl, Br, F, NO$_2$, NH$_2$, CN, CF$_3$, alkyl containing 1–4 carbon atoms, phenyl, benzoyl or OH; and (b) at least an equimolar amount of a perhalomethane selected from the group consisting of CCl$_4$, CFCl$_3$ or CBrCl$_3$; and (c) at least three molar equivalents of substantially anhydrous hydrogen fluoride.

2. The process of claim 1 wherein
   (a) the phenolic compound is reacted with
   (b) the perhalomethane being present in an amount 2–3 moles per mole of phenolic compound, and
   (c) from 20–45 moles of substantially anhydrous hydrogen fluoride per mole of phenolic compound, the reaction being carried out in the temperature range of 125° to 150° C. under autogenous pressure.

3. The process of claim 2 wherein said phenolic compound is selected from the group 3-nitrophenol, 4-nitrophenol, 4-chlorophenol, 4-aminophenol, or 2,4-dichlorophenol and the perhalomethane is CCl$_4$.

* * * * *